(12) United States Patent
Suau

(10) Patent No.: US 9,487,597 B2
(45) Date of Patent: *Nov. 8, 2016

(54) ALKALI SWELLABLE ACRYLIC EMULSIONS WITHOUT SURFACTANTS, USE THEREOF IN AQUEOUS FORMULATIONS, AND FORMULATIONS CONTAINING THEM

(75) Inventor: Jean-Marc Suau, Lucenay (FR)

(73) Assignee: COATEX S.A.S., Genay (FR)

( * ) Notice: Subject to any disclaimer, the term of this patent is extended or adjusted under 35 U.S.C. 154(b) by 405 days.

This patent is subject to a terminal disclaimer.

(21) Appl. No.: 13/160,558

(22) Filed: Jun. 15, 2011

(65) Prior Publication Data

US 2011/0319500 A1 Dec. 29, 2011

Related U.S. Application Data

(60) Provisional application No. 61/360,078, filed on Jun. 30, 2010.

(30) Foreign Application Priority Data

Jun. 25, 2010 (FR) ..................... 10 55080

(51) Int. Cl.

| | | |
|---|---|---|
| A61K 47/32 | (2006.01) | |
| C08L 41/00 | (2006.01) | |
| C08L 43/00 | (2006.01) | |
| C09D 141/00 | (2006.01) | |
| C08F 2/22 | (2006.01) | |
| C04B 24/16 | (2006.01) | |
| C04B 24/26 | (2006.01) | |
| C09D 7/00 | (2006.01) | |
| C09D 133/14 | (2006.01) | |
| C11D 3/37 | (2006.01) | |
| D21H 19/24 | (2006.01) | |
| C08F 220/18 | (2006.01) | |
| A61Q 19/00 | (2006.01) | |
| A61K 8/81 | (2006.01) | |
| C04B 103/00 | (2006.01) | |
| C04B 103/44 | (2006.01) | |
| C08F 220/06 | (2006.01) | |
| C08F 220/58 | (2006.01) | |

(52) U.S. Cl.
CPC .............. *C08F 2/22* (2013.01); *A61K 8/8158* (2013.01); *A61Q 19/00* (2013.01); *C04B 24/163* (2013.01); *C04B 24/2641* (2013.01); *C08F 220/18* (2013.01); *C09D 7/002* (2013.01); *C09D 133/14* (2013.01); *C11D 3/378* (2013.01); *D21H 19/24* (2013.01); *A61K 2800/10* (2013.01); *A61K 2800/48* (2013.01); *C04B 2103/005* (2013.01); *C04B 2103/44* (2013.01); *C08F 220/06* (2013.01); *C08F 220/58* (2013.01)

(58) Field of Classification Search
CPC .... A61K 47/32; A61Q 19/00; C04B 24/163; C09D 7/002; C09D 133/14; C11D 3/378; C08F 2/22; C08F 220/18; C08F 220/06; C08F 220/12; C08F 220/58; C08L 41/00
USPC .................................. 514/772.6; 524/3, 547
See application file for complete search history.

(56) References Cited

U.S. PATENT DOCUMENTS

| | | | | |
|---|---|---|---|---|
| 5,516,432 A | * | 5/1996 | King et al. .................... | 210/701 |
| 6,063,857 A | * | 5/2000 | Greenblatt et al. ........... | 524/561 |
| 2003/0073777 A1 | * | 4/2003 | Eknoian et al. .............. | 524/502 |
| 2006/0275240 A1 | | 12/2006 | Polotti et al. | |
| 2007/0088120 A1 | | 4/2007 | Zecha et al. | |
| 2009/0305934 A1 | * | 12/2009 | Creamer et al. .............. | 510/221 |

FOREIGN PATENT DOCUMENTS

| | | |
|---|---|---|
| CA | 2 090 343 C | 9/1993 |
| CN | 1951996 A | 4/2007 |
| EP | 0 562 344 A1 | 9/1993 |
| EP | 1 777 241 B1 | 12/2008 |
| WO | WO 2004/063228 A1 | 7/2004 |

OTHER PUBLICATIONS

U.S. Appl. No. 13/150,447, filed Jun. 1, 2011, Suau.
International Search Report issued Jul. 26, 2011, in Patent Application No. PCT/IB2011/001341(with Translation of Categories of Cited Documents).
Combined Chinese Office Action and Search Report issued Jan. 13, 2014, in Chinese Patent Application No. 201180030904.3 (English translation only).

* cited by examiner

*Primary Examiner* — Alexa Neckel
*Assistant Examiner* — Marie Reddick
(74) *Attorney, Agent, or Firm* — Oblon, McClelland, Maier & Neustadt, L.L.P.

(57) ABSTRACT

The present invention pertains to new alkali swellable thickening emulsions, free of surfactants and solvents other than water: as a result, all drawbacks related to the use of solvents, or to the formation of foam in the case of surfactants, are avoided. These new emulsions contain a certain quantity of 2-acrylamido-2-methylpropane sulfonic acid (or AMPS, CAS #: 40623-75-4). They have proven effective at thickening aqueous mediums, particularly water-based paints, paper coatings, aqueous suspensions of mineral materials, detergents, cosmetic formulations, or formulations containing a hydraulic binder.

20 Claims, No Drawings

ALKALI SWELLABLE ACRYLIC EMULSIONS WITHOUT SURFACTANTS, USE THEREOF IN AQUEOUS FORMULATIONS, AND FORMULATIONS CONTAINING THEM

REFERENCE TO PRIOR APPLICATIONS

This application claims priority to U.S. provisional application Ser. No. 61/360,078, filed Jun. 30, 2010; and to French patent application 10 55080, filed Jun. 25, 2010, both incorporated herein by reference.

FIELD OF THE INVENTION

The present invention pertains to new alkali swellable thickening emulsions, free of surfactants and solvents other than water: as a result, all drawbacks related to the use of solvents, and/or to the formation of foam in the case of surfactants, are avoided. These new emulsions contain 2-acrylamido-2-methylpropane sulfonic acid (or AMPS, CAS #: 40623-75-4). They have proven effective at thickening aqueous mediums, particularly water-based paints, paper coatings, aqueous suspensions of mineral materials, detergents, cosmetic formulations, and formulations containing a hydraulic binder.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

BACKGROUND OF THE INVENTION

Controlling the rheology of aqueous formulations that may contain mineral loads is a necessity, not just during the stage of manufacturing these products, but also during their transportation, storage, or implementation. The diversity of the practical constraints within each of these steps is due to a variety of different rheological behaviors. For example, in a paint, the need of the person skilled in the art may be summarized as the need to obtain a paint-thickening effect, for reasons of stability over time as well as for possible application of the paint onto a vertical surface, the absence of splattering at the time of implementation, or of sagging after implementation, etc.

As a result, products which contribute to this regulation of rheological behavior are designated using the term thickeners. Present in the water-based paint sector, they are also found in paper coatings, suspensions of mineral materials, detergents, cosmetic formulations, and concretes and cements. Among these thickeners, the person skilled in the art has long been aware of the particular category of alkali swellable acrylic emulsions, which are direct-emulsion polymers in water based on surfactants, said polymers being made up of at least one non-water-soluble monomer and at least one alkali swellable water-soluble monomer including methacrylic acid.

As used herein, the expression "direct emulsion of a polymer in water" designates a stable and homogenous dispersion of polymer particles in water (no reference is made here to oil-in-water or water-in-oil emulsions, which involve the existence of two separate phases, one aqueous and the other one oily). Meanwhile, the expression "swellable alkali polymer" as used herein means that the polymer is capable, whenever the medium is alkaline, of incorporating a quantity of water such that a gel forms and therefore the viscosity is improved.

There are two major families of swellable alkali acrylic thickeners: ASE (Alkali Swellable Emulsion) thickeners and HASE (Hydrophobically-modified Alkali Swellable Emulsion) thickeners. The former refer to copolymers of methacrylic acid with a non-water-soluble ester of that acid, and the latter refer to copolymers based on methacrylic acid, a non-water-soluble ester of (meth)acrylic acid, and a monomer having so-called "associative" hydrophobic groups. These copolymers may also be cross-linked.

These chemicals' mechanisms of action differ. ASE polymers thicken only in a neutral state, hence the expression "alkali-swellable": the result is an ionic repulsion mechanism between the various carboxylate groups carried by the polymer chain. These ionized groups polarize the water molecules, which cause the viscosity of the medium to increase. In addition to the aforementioned ionic phenomenon, HASE polymers involve interactions between the associative hydrophobic groups, which also contributes to thickening the medium. These mechanisms, and particularly the alkali-swellable nature of these emulsions and their ability to thicken an aqueous environment at a pH near neutral, have been described in the documents WO 2007/144721 and "Practical guide to associative thickeners" (Proceedings of the Annual Meeting Technical Program of the FSCT, 2000, 78th, 644-702).

Many applications of these thickeners are found in paints, paper coatings, and cosmetics (see patent applications FR 2,693,203 A1, FR 2,872,815 A1, FR 2,633,930 A1, FR 2,872,815 A1). Furthermore, they exist in commercial form, particularly by way of the product lines Rheocarb™, Rheocoat™, Thixol™, Rheotech™, Polyphobe™ and Viscoatex™ sold by the company COATEX™ S.A.S.

Generally speaking, ASE and HASE thickeners are manufactured in the form of direct emulsions of the alkali-swellable polymer in water, whose active ingredient content oscillates between 10% and 45% of their total weight.

The corresponding synthesis process is particularly described in the following publications: "Synthesis of an alkali-swellable emulsion and its effect on the rate of polymer diffusion in poly(vinyl acetate-butyl acrylate) latex films" (Journal of Polymer Science, Part A: Polymer Chemistry, 2005, 43 (22), pp. 5632-5642), "Structural and rheological properties of hydrophobically modified alkali-soluble emulsion solutions" (Journal of Polymer Science, Part B: Polymer Physics, 2002, 40(18), pp. 1985-1994), "Viscoelastic properties of hydrophobically modified alkali-soluble emulsion in salt solutions" (Polymer, 1999, 40 (23), pp. 6369-6379), "Dissolution behavior in water of a model hydrophobic alkali-swellable emulsion polymer with $C_{20}H_{41}$ groups" (Canadian Journal of Chemistry, 1998, 76 (11), pp. 1779-1787).

Many patent applications have also covered it (EP 0,089,213 A1, EP 0 646,606 A1, EP 0,979,833 A1 for ASE, and EP 0,013,836 A1, WO 93/2454 A1, U.S. Pat. No. 4,268,641 A1, U.S. Pat. No. 4,421,902 A1, U.S. Pat. No. 3,915,921 A1 for HASE).

One constant of their manufacturing method resides in the implementation of surfactants, whose first function is to stabilize the polymer particles suspended in water. Surface-active agents well-known for this use are sodium lauryl sulfate, dodecylbenzene sulfonate, and ethoxylated fatty alcohol sulfates. Though their implementation has been described for 30 years (see document EP 0,013,836 cited above, page 7, lines 3-12), this implementation still appears in much more recent documents, like the scientific publications listed above.

The use of surfactants therefore appears to be an unavoidable characteristic in methods for manufacturing ASE and HASE emulsions. However, there is a tendency to omit or ignore the drawbacks engendered by these surfactants, as it is believed that their use cannot be eliminated. These problems are first and foremost linked to the natural formation of foam, starting when the medium containing the surfactant is stirred: besides aesthetic drawbacks, this foam may degrade the thickener's efficiency.

In the case of a paint, it may create unevenness within the aqueous formulation, and even alter the properties of the end product, meaning the dry paint film resulting from the drying of the aqueous formulation. The formation of "craters" or insoluble particles may thereby be observed; these are just some of the heterogeneities that harm the aesthetic aspect and surface properties of the film (the mechanical aspect, as well as the optical properties and surface condition). Finally, it is well-known that the presence of surfactants in a paint formulation will ultimately degrade the soapable nature of the dry film (see "Effect of surfactants used for binder synthesis on the properties of latex paints", Progress in Organic Coatings, 2005, 53 (2), pp. 112-118).

SUMMARY OF THE INVENTION

In order to remedy such drawbacks, the present inventor has engineered a new method for manufacturing emulsions, particularly ASE and HASE emulsions, which does not involve any surfactants, nor any solvents other than water. One characteristic of this method is that it implements, besides the normal monomers to be polymerized e.g., in ASE and HASE emulsions, a certain quantity of a particular monomer, which is 2-acrylamido-2-methylpropane sulfonic acid (or AMPS, CAS #: 40623-75-4). Entirely surprisingly and advantageously, the result in a preferred embodiment is the manufacturing of genuine ASE and HASE emulsions, each exhibiting a commercial solids content (greater than 25% by dry weight of the active ingredient), which are stable over time, characterized by particle sizes similar to emulsions of the prior art, whose thickening effectiveness is proven.

It has already been known how to polymerize AMPS in an emulsion with (meth)acrylic monomers and their esters, but this technique had always been described in the presence of surfactants (see, for example, the document U.S. Pat. No. 3,931,087 A1). Other examples of copolymers are found which contain a carboxylic acid (like acrylic acid) with AMPS, but still in the presence of surfactants or solvents other than water; however, it is clear that the solvents currently exhibit a very large number of drawbacks with regard to the preservation of the environment. Examples of such products exist in the field of cement (EP 1,886,980 A1), pharmacy (EP 1,400 564 A1), and ceramics (EP 1,262 463 A1), though without them being alkali-swellable, much less alkali-swellable emulsions exhibiting an associative nature.

In the field of alkali-swellable emulsions, AMPS had already been conceived of as a co-monomer; on the other hand, nobody had yet thought that the surfactants were not necessary to the synthesis of the polymer containing it, and nobody had been able to detect the influence that this could have on the manufacture of ASE and HASE emulsions.

By way of example, the documents WO 03/012004 A1 and WO 03/012004 A1 describe HASE thickening emulsions incorporating AMPS, but whose synthesis is carried out in the presence of surfactants and/or solvents other than water. The documents FR 2,873,126 A1 and FR 2,782,086 A1 describe inverse oil/water emulsions created with emulsifying agents, a copolymer of AMPS with (meth)acrylic acid, and another monomer which may be an ester of these acids.

Finally, all of the literature dealing with the manufacturing of emulsions without surfactants could not guide the person skilled in the art on the implementation of AMPS. Instead, it was mainly centered on particular methods such as acoustic waves, super-critical $CO_2$ ("Surfactant-free emulsions", Current opinion in Colloidal and Interface Science, 13, 2008, pp. 228-235), controlled radical polymerization ("Surfactant-Free, Controlled/Living Radical Emulsion Polymerization in batch conditions using a low molar mass RAFT Agent", Macromolecules, 2008, 41 (21), pp 7850-7856), or in miniemulsions ("Emulsifier-free mini-emulsion polymerization of styrene and the investigation of encapsulation of nanoparticles with polystyrene via this procedure using an anionic initiator", Journal of Applied Polymer Science, 105, 3, pp. 1244-1250). It goes without saying that the inventive method is simple to an extent unparalleled by the techniques listed above.

Consequently, the ASE and HASE which result from the inventive method, and which are in the form of direct emulsions free of surfactants and solvents other than water, are themselves new and exhibit the advantage of not forming any foam when stirred, unlike their predecessors.

DETAILED DESCRIPTION OF THE PREFERRED EMBODIMENTS

One object of the present invention is a method for manufacturing a direct emulsion of a polymer in water comprising the polymerization of, expressed as a % by weight of each of the monomers, monomer group A and, separately, monomer group B, in a polymerization medium comprising water:

Monomer Group A:
  a) 20% to 60% by weight of at least one of methacrylic acid and acrylic acid,
  b) 40% to 80% by weight of at least one ester of (meth)acrylic acid,
  c) 0.05% to 22% by weight of 2-acrylamido-2-methylpropane sulfonic acid,
  d) 0 to 1% by weight of at least one cross-linking monomer,
  the total a)+b)+c)+d) being equal to 100%, Monomer Group B:
  a) 20% to 60% by weight of at least one of methacrylic acid and acrylic acid,
  b) 40% to 80% by weight of at least one ester of (meth)acrylic acid,
  c) 0.5% to 25% by weight of a monomer containing a hydrophobic group,
  d) 0.05% to 22% by weight of 2-acrylamido-2-methylpropane sulfonic acid,
  e) 0 to 1% by weight of at least one cross-linking monomer,
  the total a)+b)+c)+d)+e) being equal to 100%, In both cases the polymerization medium is free of surfactants (other than 2-acrylamido-2-methylpropane sulfonic acid to the extent AMPS is considered a surfactant) and solvents other than water.

Other characteristics of this method (temperature, choice of catalytic system, implementation of a transfer agent, potential use of cross-linking, etc.) are within the skill of the ordinary artisan in view of this disclosure and can include the ones described in the state of the art, particularly in the aforementioned documents, to which the person skilled in the art may refer.

In a preferred embodiment the ester of (meth)acrylic acid is chosen from among ethyl acrylate, butyl acrylate, methyl methacrylate, and mixtures thereof.

In a preferred embodiment the monomer containing a hydrophobic group possesses the general formula:

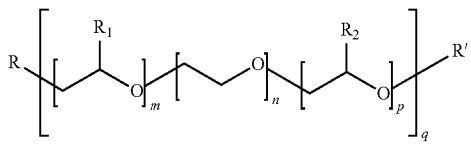

where:
- m, n, p and q are integers and m, n, p are less than 150, q is greater than 0, and at least one integer among m, n and p is nonzero;
- R has a polymerizable vinylic function,
- $R_1$ and $R_2$ are identical or different, and represent hydrogen atoms or alkyl groups,
- R' is a hydrophobic group comprising at least 6 and at most 36 carbon atoms.

In a preferred embodiment the cross-linking monomer is chosen fromethylene glycol dimethacrylate, trimethylolpropanetriacrylate, diallyl phthalate, allyl acrylate, allyl maleates, methylene-bis-acrylamide, methylene-bis-methacrylamide, tetrallyloxyethane, triallylcyanurates, and allylic ethers obtained from polyols.

In a preferred embodiment the aqueous emulsion exhibits a solids content of between 10% and 50% by dry weight of polymer, in relation to its total weight.

In a preferred embodiment the emulsion exhibits a particle size of between 50 nm and 500 nm.

In a preferred embodiment the polymer exhibits an average molar mass by weight of between 20,000 g/mol and 1,000,000 g/mol.

A further object of the present invention is a direct emulsion of a polymer in water, optionally prepared according to the above method, wherein the polymer is made up of, expressed as a % by weight of each of the monomers, polymerized monomer units of monomer group A and, separately, monomer group B:

Monomer Group A:
- a) 20% to 60% by weight of at least one of methacrylic acid and acrylic acid,
- b) 40% to 80% by weight of at least one ester of (meth)acrylic acid,
- c) 0.05% to 22% by weight of 2-acrylamido-2-methylpropane sulfonic acid,
- d) 0 to 1% by weight of at least one cross-linking monomer, the total a)+b)+c)+d) being equal to 100%, Monomer Group B:
- a) 20% to 60% by weight of at least one of methacrylic acid and acrylic acid,
- b) 40% to 80% by weight of at least one ester of (meth)acrylic acid,
- c) 0.5% to 25% by weight of the monomer containing a hydrophobic group,
- d) 0.05% to 22% by weight of 2-acrylamido-2-methylpropane sulfonic acid,
- e) 0 to 1% by weight of at least one cross-linking monomer, the total a)+b)+c)+d)+e) being equal to 100%, In each case (i.e, a direct emulsion of polymerized monomer units of monomer group A and a direct emulsion of polymerized monomer units of monomer group B) the direct emulsion is free of surfactants (other than 2-acrylamido-2-methylpropane sulfonic acid to the extent AMPS is considered a surfactant) and solvents other than water.

In a preferred embodiment the monomer containing at least one hydrophobic group has the general formula:

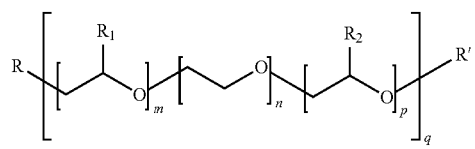

where:
- m, n, p and q are integers and m, n, p are less than 150, q is greater than 0, and at least one integer among m, n and p is nonzero;
- R has a polymerizable vinylic function,
- $R_1$ and $R_2$ are identical or different, and represent hydrogen atoms or alkyl groups,
- R' is a hydrophobic group comprising at least 6 and at most 36 carbon atoms.

In a preferred embodiment the cross-linking monomer is chosen fromethylene glycol dimethacrylate, trimethylolpropanetriacrylate, diallyl phthalate, allyl acrylate, allyl maleates, methylene-bis-acrylamide, methylene-bis-methacrylamide, tetrallyloxyethane, triallylcyanurates, and allylic ethers obtained from polyols.

In a preferred embodiment the emulsion exhibits a solids content of between 10% and 50% by dry weight of polymer, in relation to its total weight.

In a preferred embodiment the polymer has a particle size between 50 nm and 500 nm.

In another preferred embodiment the polymer exhibits an average molar mass by weight of between 20,000 g/mol and 1,000,000 g/mol.

A further object of the present invention resides in the use of the aforementioned emulsion, as a thickening agent of an aqueous formulation, and the formulation produced. Concretely, the emulsion is added into the medium to be thickened, whose pH is regulated to be nearly neutral, in order to achieve the thickening effect. The person skilled in the art, from routine experience and in view of this disclosure, will know how to find the pH from which the thickening phenomenon is observed.

Preferred formulations including the invention direct emulsions are chosen from among an aqueous paint, a paper coating, an aqueous suspension of mineral materials, a detergent, a cosmetic formulation, and a formulation containing a hydraulic binder.

Another preferred object of the present invention resides in an aqueous formulation containing the aforementioned emulsion, said formulation being chosen from among a water-based paint, a paper coating, an aqueous suspension of mineral materials, a detergent, a cosmetic formulation, or containing a hydraulic binder.

In embodiments herein where 20% to 60% by weight of at least one of methacrylic acid and acrylic acid is specified and both are present the weight amounts of methacrylic acid to acrylic acid can range from less than 1: more than 99-more than 99: less than 1 and include 5:95-95:5; 15:85-85:15, 40:60-60:40; 50:50, etc.

EXAMPLES

Example 1

This example concerns the synthesis of various ASE and HASE emulsions, without surfactants and without solvents other than water.

Test #1 According to the Invention

This test concerns the fabrication of an ASE emulsion, containing a copolymer made up of, expressed as a % by weight of each of its monomers:
a) 36.5% methacrylic acid,
b) 62.3% ethyl acrylate,
c) 1.2% of AMPS.

In a 1 liter reactor equipped with mechanical agitation and an oil-bath heating system, 605 g of bipermutated water and 7.5 g of a solution of AMPS are added (a 55% solution of sodium hydroxide-neutralized AMPS in water, sold by the company LUBRIZOL™ under the name AMPS 2405).

The medium is heated to 82° C., then the catalytic system made up of 1.0 g of ammonium persulfate dissolved in 10 g of bipermutated water and 0.1 g of sodium metabisulfite dissolved in 10 g of bipermutated water is added through a funnel.

Next, 215 g of ethyl acrylate and 140 g of methacrylic acid (90% solution) are then continuously and gradually added.

Throughout the entire addition process, the reaction medium's temperature is kept at 85° C. (±2).

Once adding is complete, the pump is rinsed with 15 g of bipermutated water, then it is left to react for 30 minutes at 85° C. (±2).

Next, 0.15 g of ammonium persulfate dissolved in 20 g of water is added in 30 minutes while keeping the temperature at 85° C. (±2) and it is left to react for 1 hour at 87° C. (±2).

The result is a perfectly homogeneous emulsion containing 34.0% by weight of solids content, whose particle size, measured by dynamic light scattering, is equal to 170 nm.

Comparative Tests

It was first sought to manufacture the same polymer as in test 1, but without implementing AMPS, i.e. a polymer made up of 36.5% by weight of methacrylic acid and 63.5% by weight of ethyl acrylate.

To do so, the same protocol was implemented as before, except for the initial addition of AMPS. After having been allowed to react at 85° C. for 1 hour, the formation of a cloudy precipitate in the solution is observed, part of which is fixed on the reactor's axis (scaling). The size of the particles formed is about 400 nm. The medium which is very non-homogeneous and rich in large particles, is not suitable for handling, particularly for pumping operations. Storage might lead to sedimentation of the product.

Next, a quantity of AMPS greater than 22% by weight of the total mass of the involved monomers, using a procedure identical to the one described in test #1, is implemented, the copolymer then being made up, expressed as a % by weight of each of its monomers:

a) 36.5% methacrylic acid,
b) 38.5% ethyl acrylate,
c) 25.0% of AMPS.

Next, the formation of insoluble species that precipitate into the medium are observed.

The AMPS (1.2%, weight for weight) was then replaced by another monomer implemented in the ASE and HASE emulsions: either acrylic acid, or methacrylic acid, or an ester which is ethyl acrylate. Homogeneous emulsions are not achieved; the observations are the same as before, with the formation of a precipitate, the scaling phenomenon, and the harmful consequences that ensue.

Next, AMPS (still 1.2% weight for weight) was replaced with styrene, lauryl methacrylate, 2-sulfoethyl methacrylate, sodium styrene sulfonate, sodium salt of 1-allyloxy-2-hydroxypropyl sulfonate (Sipomer COPS 1), achieving identical results (insolubles present, and scaling phenomenon).

Tests #2 to 11 According to the Invention

Tests #2 to 11 relate to the synthesis of other emulsions illustrating the invention, according to the same procedure as described above.

Tests #2 to 8 illustrate other monomer compositions with an AMPS mass rate set to 1.2%, while tests #9 to 11 illustrate other AMPS levels (the mass ratio between ethyl acrylate and methacrylic acid has been kept constant).

Perfectly homogeneous emulsions are achieved, whose characteristics appear in table 1.

TABLE 1

| Test # | Monomer composition (% by mass) | Solids content (%) | Particle diameter (nm) |
|---|---|---|---|
| 2 | 1.2 AMPS/62.3 EA/36.5 MAA | 34.0 | 212 |
| 3 | 1.2 AMPS/74.6 EA/18.5 AA/5.7 MAA | 32.3 | 214 |
| 4 | 1.2 AMPS/68.7 EA/18.6 AA/11.5 MAA | 32.1 | 115 |
| 5 | 1.2 AMPS/61.3 EA/1.7 AA/35.8 MAA | 32.1 | 198 |
| 6 | 1.2 AMPS/60.3 EA/3.3 AA/35.2 MAA | 33.1 | 198 |
| 7 | 1.2 AMPS/53.25 EA/28.9 AA/6.9 MAA/ 9.75 MethC22OE25 | 38.5 | 183 |
| 8 | 1.2 AMPS/62.2 EA/28.5 AA/3.3 MAA/ 4.8 MethC22OE25 | 38.5 | 153 |
| 9 | 10 AMPS/57.9 EA/32.1 MAA | 34.0 | 220 |
| 10 | 15 AMPS/55.4 EA/29.6 MAA | 34.0 | 280 |
| 11 | 20 AMPS/52.9 EA/27.1 MAA | 34.0 | 319 |

In this table, MethC22OE25 designates a monomer with formula (I) in which R designates the methacrylate function, $m=p=0$, $n=25$, and R' designates a methyl group, EA designates ethyl acrylate, and AA and MAA respectively designate acrylic and methacrylic acids.

Example 2

This example illustrates the thickening power of the inventive emulsions implemented in water in such a way as to have an active ingredient level of 5% by dry polymer weight. After being added to water, the medium is neutralized by adding sodium hydroxide at a pH of around 6.5, and the Brookfield™ viscosity of the medium is measured, at 25° C. and at 100 revolutions/minute, whose values are listed in table 2

TABLE 2

| Emulsion according to test # | Brookfield ™ viscosity (mPa · s) of the gel at 5% |
|---|---|
| 1 | 3420 |
| 8 | 2920 |

TABLE 2-continued

| Emulsion according to test # | Brookfield ™ viscosity (mPa · s) of the gel at 5% |
|---|---|
| 9 | 1880 |
| 10 | 1440 |

The thickening nature of the manufactured emulsions is thereby demonstrated, starting when they are placed in aqueous solution and under alkaline conditions.

Example 3

This example illustrates the implementation, in formulating a concrete, of commercial ASE thickeners (containing surfactants) and an inventive emulsion free of surfactants.

To do so, a concrete is produced using techniques well-described in the literature, made up of:
300 kg of CEM I 52.5 N cement;
880 of large 10/20 gravel;
110 kg of 0/4 sand;
whose water-to-cement ratio W/C is set to 0.5, and into which the following are added, in relation to the cement's dry weight:
  1.23% by weight as-is of a dispersing agent sold by the company COATEX™ under the name Ethacryl™ 1030;
  1% by weight as-is of an anti-foaming agent sold by the company HUNTSMANN™ under the name Empilan™ PF 7169.

Tests A, B, C, and D, respectively implement 0.7% by-weight as is in the concrete formulation:
  an ASE emulsion containing surfactants sold by the company COATEX™ under the name Viscoatex™ 730;
  an ASE emulsion containing surfactants sold by the company COATEX™ under the name Viscoatex™ 35;
  an HASE emulsion containing surfactants sold by the company COATEX™ under the name Viscoatex™ 66;
  an emulsion according to the invention, which is described in test #1.

For each test A, B, C and D, the entrained air is measured, according to the EN 12350-7 standard. 9.5%, 12.0%, 12.5%, and 2.5% are respectively achieved.

The thickening emulsion therefore makes it possible to considerably reduce the quantity of air added into the formulation. The end result is therefore a product which is more compact, with improved resistance.

As mentioned above, as used herein, the expression "direct emulsion of a polymer in water" designates a stable and homogenous dispersion of polymer particles in water (no reference is made here to oil-in-water or water-in-oil emulsions, which involve the existence of two separate phases, one aqueous and the other one oily). Meanwhile, the expression "swellable alkali polymer" as used herein means that the polymer is capable, whenever the medium is alkaline, of incorporating a quantity of water such that a gel forms and therefore the viscosity is improved.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for manufacturing a direct emulsion of a polymer in water, comprising polymerizing monomer group B in a polymerization medium consisting of water and catalyst:
  wherein monomer group B consists of:
    a) 20% to 60% by weight of at least one of methacrylic acid and acrylic acid,
    b) 40% to 80% by weight of at least one ester of (meth)acrylic acid,
    c) 0.5% to 25% by weight of a monomer comprising at least one hydrophobic group,
    d) 0.05% to 22% by weight of 2-acrylamido-2-methyl-propane sulfonic acid, and
    e) 0 to 1% by weight of at least one cross-linking monomer,
  provided that the total of a)+b)+c)+d)+e) is equal to 100%,
  and
  wherein the monomer comprising at least one hydrophobic group has the formula (I):

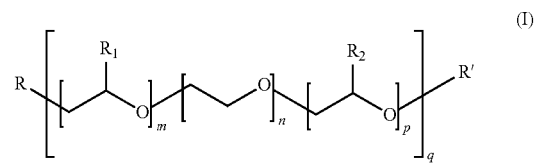

where:
  m, n, p and q are integers and m, n, and p are less than 150, q is greater than 0, and at least one integer among m, n and p is nonzero;
  R has a polymerizable vinyl function,
  $R_1$ and $R_2$ are identical or different, and represent hydrogen atoms or alkyl groups,
  R' is a hydrophobic group comprising at least 6 and at most 36 carbon atoms.

2. The method according to claim 1, wherein the ester of (meth)acrylic acid is selected from the group consisting of ethyl acrylate, butyl acrylate, methyl methacrylate, and mixtures thereof.

3. The method according to claim 1, wherein the cross-linking monomer is present and is selected from the group consisting of ethylene glycol dimethacrylate, trimethylolpropanetriacrylate, diallyl phthalate, allyl acrylate, allyl maleates, methylene-bis-acrylamide, methylene-bis-methacrylamide, tetrallyloxyethane, triallylcyanurates, allylic ethers obtained from polyols, and mixtures thereof.

4. The method according to claim 1, wherein the emulsion has a solids content of 10%-50% by weight in relation to the total weight of the emulsion.

5. The method according to claim 1, wherein polymer particles in the emulsion have a particle size between 50 nm and 500 nm.

6. The method according to claim 1, wherein the polymer has a $M_w$ of 20,000 g/mol-1,000,000 g/mol.

7. The method according to claim 1, wherein the ester of (meth)acrylic acid is selected from the group consisting of ethyl acrylate, butyl acrylate, methyl methacrylate, and mixtures thereof;
the cross-linking monomer is present and is selected from the group consisting of ethylene glycol dimethacrylate, trimethylolpropanetriacrylate, diallyl phthalate, allyl acrylate, allyl maleates, methylene-bis-acrylamide, methylene-bis-methacrylamide, tetrallyloxyethane, triallylcyanurates, allylic ethers obtained from polyols, and mixtures thereof;
the emulsion has a solids content of 10%-50% by weight in relation to the total weight of the emulsion;
polymer particles in the emulsion have a particle size between 50 nm and 500 nm; and
the polymer has a $M_w$ of 20,000 g/mol-1,000,000 g/mol.

8. The method according to claim 1, wherein the cross-linking monomer is present in monomer group B.

9. A direct emulsion of a polymer in water, consisting of water, catalyst and polymer, wherein said polymer consists of polymerized monomers of monomer group B:
wherein monomer group B consists of:
a) 20% to 60% by weight of at least one of methacrylic acid and acrylic acid,
b) 40% to 80% by weight of at least one ester of (meth)acrylic acid,
c) 0.5% to 25% by weight of the monomer comprising at least one hydrophobic group,
d) 0.05% to 22% by weight of 2-acrylamido-2-methyl-propane sulfonic acid, and
e) 0 to 1% by weight of at least one cross-linking monomer,
provided that the total of a)+b)+c)+d)+e) is equal to 100%,
and
wherein the monomer comprising at least one hydrophobic group has the formula (I):

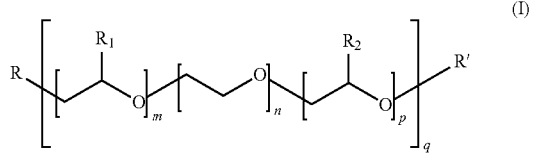

where:
m, n, p and q are integers and m, n, and p are less than 150, q is greater than 0, and at least one integer among m, n and p is nonzero;
R has a polymerizable vinyl function,
$R_1$ and $R_2$ are identical or different, and represent hydrogen atoms or alkyl groups,
R' is a hydrophobic group comprising at least 6 and at most 36 carbon atoms.

10. The direct emulsion as claimed in claim 9, wherein the cross-linking monomer is present and is selected from the group consisting of ethylene glycol dimethacrylate, trimethylolpropanetriacrylate, diallyl phthalate, allyl acrylate, allyl maleates, methylene-bis-acrylamide, methylene-bis-methacrylamide, tetrallyloxyethane, triallylcyanurates, allylic ethers obtained from polyols, and mixtures thereof.

11. The direct emulsion as claimed in claim 9, having a solids content of 10%-50% by weight in relation to the total weight of the emulsion.

12. The direct emulsion as claimed in claim 9, wherein polymer particles in the emulsion have a particle size of 50 nm-500 nm.

13. The direct emulsion as claimed in claim 9, wherein the polymer has a $M_w$ of 20,000 g/mol-1,000,000 g/mol.

14. A method, comprising adding the direct emulsion as claimed in claim 9 to an aqueous formulation.

15. The method according to claim 14, wherein said formulation is selected from the group consisting of an aqueous paint, a paper coating, an aqueous suspension of mineral materials, a detergent, a cosmetic formulation, and a formulation containing a hydraulic binder.

16. An aqueous formulation comprising the direct emulsion as claimed in claim 9.

17. The formulation according to claim 16, wherein the aqueous formulation is selected form the group consisting of a water-based paint, a paper coating, an aqueous suspension of mineral materials, a detergent, a cosmetic formulation, and a formulation containing a hydraulic binder.

18. The direct emulsion as claimed in claim 9, wherein:
the direct emulsion has a solids content of 10%-50% by weight in relation to the total weight of the emulsion,
the polymer particles in the emulsion have a particle size of 50 nm-500 nm, and
the polymer has a $M_w$ of 20,000 g/mol-1,000,000 g/mol.

19. The direct emulstion according to claim 9, wherein the cross-linking monomer is present in monomer group B.

20. The direct emulsion as claimed in claim 9, wherein:
the cross-linking monomer is present and is selected from the group consisting of ethylene glycol dimethacrylate, trimethylolpropanetriacrylate, diallyl phthalate, allyl acrylate, allyl maleates, methylene-bis-acrylamide, methylene-bis-methacrylamide, tetrallyloxyethane, triallylcyanurates, allylic ethers obtained from polyols, and mixtures thereof;
the direct emulsion has a solids content of 10%-50% by weight in relation to the total weight of the emulsion;
polymer particles in the emulsion have a particle size of 50 nm-500 nm; and
the polymer has a $M_w$ of 20,000 g/mol-1,000,000 g/mol.

* * * * *